US008313695B2

(12) United States Patent
Akutsu (10) Patent No.: US 8,313,695 B2
(45) Date of Patent: Nov. 20, 2012

(54) AUTOMATIC ANALYZER (75) Inventor: Masashi Akutsu, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/094,129

(22) Filed: Apr. 26, 2011

(65) Prior Publication Data
US 2011/0200485 A1 Aug. 18, 2011

Related U.S. Application Data (62) Division of application No. 12/038,389, filed on Feb. 27, 2008, now abandoned.

(30) Foreign Application Priority Data

Feb. 28, 2007 (JP) .................................. 2007-048387

(51) Int. Cl.
G01N 21/00 (2006.01)
G01N 31/00 (2006.01)
G01N 33/00 (2006.01)
G05B 21/00 (2006.01)
(52) U.S. Cl. ................. 422/64; 422/67; 436/8; 700/266
(58) Field of Classification Search .................... 422/64, 422/67
See application file for complete search history.

(56) References Cited

U.S. PATENT DOCUMENTS

| 3,960,497 A * | 6/1976 | Acord .............................. 422/67 |
| 4,043,756 A * | 8/1977 | Sommervold .................. 436/43 |
| 4,678,755 A * | 7/1987 | Shinohara et al. .............. 436/43 |
| 5,204,264 A * | 4/1993 | Kaminer ........................... 436/8 |
| 5,424,212 A | 6/1995 | Pinsl-Ober et al. |
| 6,080,364 A * | 6/2000 | Mimura et al. .................. 422/67 |
| 6,579,717 B1 | 6/2003 | Matsubara et al. |
| 6,599,749 B1 | 7/2003 | Kodama et al. |
| 6,846,457 B1 | 1/2005 | Tokiwa et al. |
| 2004/0141882 A1 | 7/2004 | Mimura et al. |
| 2005/0037502 A1 | 2/2005 | Miller |
| 2005/0249634 A1 | 11/2005 | Devlin, Sr. |
| 2006/0245865 A1 | 11/2006 | Babson |
| 2009/0142844 A1 | 6/2009 | Le Comte |

FOREIGN PATENT DOCUMENTS

| EP | 0 445 616 A2 | 9/1991 |
| EP | 0 871 034 A2 | 10/1998 |
| EP | 1 061 372 A2 | 12/2000 |
| EP | 1 600 779 A2 | 11/2005 |
| EP | 1 762 850 A2 | 3/2007 |

(Continued)

Primary Examiner — In Suk Bullock
Assistant Examiner — Bryan Kilpatrick
(74) Attorney, Agent, or Firm — Mattingly & Malur, P.C.

(57) ABSTRACT

An automatic analyzer for performing analysis of a precision control sample in response to an external factor to alleviate the burden on the operator and perform precision control at appropriate timing, thereby allowing automatic maintenance of the measurement precision. Analysis of a precision control sample is performed by creating an analysis request for the internally held precision control sample and then transferring the precision control sample in response to an external factor occurring, when a calibrator is inputted in the analyzer, the number of remaining reagents under analysis satisfies a predetermined condition (becomes zero or falls below a specified value), the date changes, a specified time runs out, the operator is changed, the number of analyzed samples exceeds a specified value, a specified time period has elapsed, a new reagent is registered, and a measurement failure is detected.

4 Claims, 8 Drawing Sheets

FOREIGN PATENT DOCUMENTS

| | | |
|---|---|---|
| EP | 1 835 291 A2 | 9/2007 |
| EP | 1 895 307 A1 | 3/2008 |
| FR | 2 888 328 A1 | 1/2007 |
| JP | 10-325839 | 12/1998 |

* cited by examiner

AUTOMATIC ANALYZER

This application is a divisional of U.S. patent application Ser. No. 12/038,389, filed Feb. 27, 2008, which claims priority to Japanese Patent Application No. 2007-048387, filed Feb. 28, 2007, and which is incorporated herein by reference in its entirety.

BACKGROUND OF THE INVENTION

1. Field of the Invention

The present invention relates to an automatic analysis system which performs qualitative and quantitative analyses of a biological sample, such as blood, urine, etc. More particularly, the present invention relates to an automatic analysis system which is provided with a transfer system for transferring sample vessels to analysis system.

2. Description of the Related Art

There is a remarkable increase in the use of automatic analyzers which automatically perform qualitative and quantitative analyses of a biological sample, such as blood, urine, etc., mainly in large hospitals and clinical inspection centers where it is necessary to process biological samples of a number of patients in a short time. Various types of automatic analyzers, i.e., large-, medium-, and small-sized automatic analyzers are under development in relation to the throughput. Particularly in the case of a certain large-sized analyzer which performs analysis of a number of samples, a sample vessel containing a biological sample is held in a holder, called sample rack, and then transferred to a plurality of analyzers through a transfer line (transfer system). When an inspection engineer inputs the sample rack into a sample rack input slot, the analyzer automatically performs processing up to output of analysis results.

In this case, the transfer line having a form of a belt conveyor transfers the sample rack inputted through the sample rack input slot, a bar code reader provided in the middle of the transfer line recognizes the rack type and sample, and then analysis is performed. As such an automatic analysis system, a system disclosed for example in JP-A-10-325839 is known.

SUMMARY OF THE INVENTION

With such a large-scale system, it is necessary to maintain the measurement precision (quantitative characteristics) of the system by placing a calibrator and a precision control sample having known concentration, etc. and periodically performing analysis. The calibrator and precision control sample are analyzed according to the order in which they are inputted into the sample rack input slot. Further, since not all items (TP, GOT, and other analysis items) can be covered with a single calibrator and a single precision control sample, measurement of a plurality of calibrators and precision control samples is necessary.

With a medium- or small-sized automatic analyzer, a sample vessel storing a sample under measurement is arranged on a disk-shaped sample disk. Therefore, it is possible for the operator of the analyzer to perform calibration and precision control simply by inputting measurement commands in the analyzer.

However, with a large-sized automatic analyzer for transferring racks by use of a transfer line, it is necessary for the operator of the analyzer to install a sample rack mounting sample vessels for storing a calibrator and a precision control sample at the rack input unit of the analyzer.

Therefore, if the operator does not input a rack mounting a calibrator and a precision control sample, calibration and precision control cannot be performed.

In such a case, the operator needs to prepare a calibrator and a precision control sample even during analysis of a general sample. This may prevent analysis of general samples which is a primary object of the analyzer.

An object of the present invention is to provide an automatic analyzer that can accomplish precision control even if the operator does not perform an operation of inputting a precision control sample.

A configuration of the present invention for accomplishing the above-mentioned object will be explained below.

An automatic analyzer comprising: an analysis unit for analyzing a biological sample; a transferring mechanism for transferring a sample rack to the analysis mechanism and a sample rack (with sample dispensing completed) from the analysis mechanism; a sample supply unit which supplies a sample to the sample buffer; and a sample storage unit which stores a sample from the sample buffer.

Although a typical transferring mechanism is structured such that a space arranging racks moves by itself, such as a belt conveyer, or a sample rack gripped by an arm or claw is slid on a base without move of the base, any transferring mechanism is possible as long as it is provided with a physically movable sample rack.

There is provided a mechanism that can keep holding a precision control sample inputted to the sample buffer.

There is provided a second sample provision unit that can keep holding a precision control sample in each analysis unit.

When a precision control sample is kept internally held, the automatic analyzer according to the present invention is capable of automatically performing analysis of a precision control sample in response to an external factor, such as, for example, when a calibrator is inputted in the analyzer, the number of remaining reagents satisfies a predetermined condition (becomes zero or falls below a specified value), the number of analyzed samples exceeds a specified value, a specified time period has elapsed, etc. Accordingly, it is possible to easily accomplish precision control at appropriate timing, thereby alleviating the burden on the operator.

DETAILED DESCRIPTION OF THE PREFERRED EMBODIMENTS

A configuration and operations of an automatic analysis system according to an embodiment of the present invention will be explained below with reference to FIGS. 1 to 9.

Figure 1:
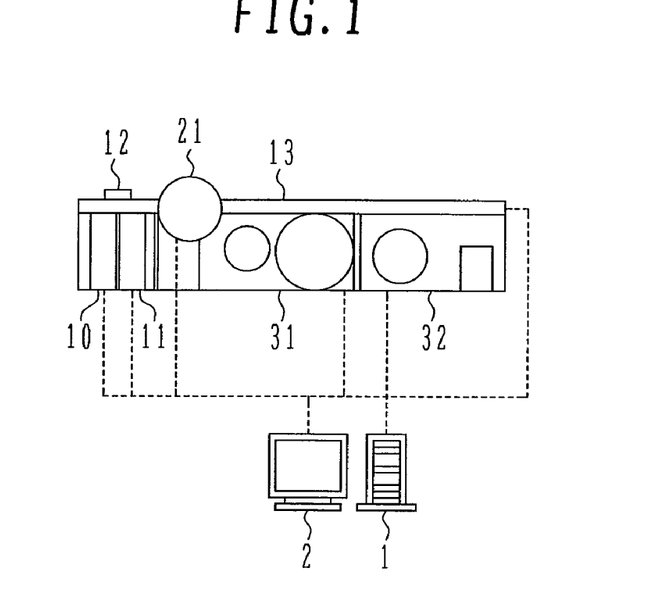
FIG. 1 is a diagram showing an embodiment of an automatic analyzer according to the present invention.

FIG. 1 is a diagram showing a general configuration of an automatic analyzer according to an embodiment of the present invention.

The automatic analysis system according to the present embodiment comprises: a sample rack input part 10; a sample rack storage part 11; an ID reader 12; a transfer line 13, a sample rack buffer unit 21; analysis modules 31 and 32; and management computers 1 and 2.

The sample rack input part 10 is used to input sample racks which holds samples. The analysis modules 31 and 32 are arranged along the transfer line 13 and removably connected to the transfer line 13. There may be any number of analysis modules. The present embodiment includes two analysis modules.

The transfer line 13 transfers a sample rack from the sample rack input part 10 to the analysis modules 31 and 32 according to an analysis request, transfers a sample rack holding a sample that has been analyzed by the analysis modules 31 and 32 to the sample rack buffer unit 21, or transfers a sample rack not requested for analysis to the sample rack storage part 11.

The sample rack buffer unit 21 provided in the transfer line 13, with which a rack storing a calibrator, a precision control sample, and a general sample are transferred, is a line mechanism that is capable of holding one or more sample racks. The sample rack buffer unit 21 makes it possible to hold a rack holding any sample transferred from the transfer line 13 for a desired time period and then resupply the sample rack to the analysis modules or the sample rack storage part 11 at desired timing.

The sample rack input part 10 includes the management computers which perform necessary control of the sample rack input part 10, the sample rack storage part 11, the ID reader 12, the transfer line 13, and the sample rack buffer unit 21. Further, a memory unit of the management computer 1 for storing input/output information and a display unit 2 for inputting information and displaying analysis results are connected to the management computers 1 and 2.

A sample held by the sample rack has a sample ID which indicates sample-related attribute information (receipt number, patient name, request analysis item, etc.) and further the sample rack has a rack ID which indicates rack identification information, such as the rack number. The sample rack placed in the sample rack input part 10 is transferred by the transfer line 13. When the sample rack is moved on the transfer line 13, the sample ID and the sample rack ID are read by the ID reader 12 and then transferred to the total management computers 1 and 2. The total management computers 1 and 2 determine an analysis module that will analyze a requested analysis item based on the attribute information.

Although a sample mentioned here is typically serum which is liquid under inspection, it is also possible to perform analysis with whole blood or diluted liquid sample. Further, a sample rack means a rack in which one or more sample vessels for storing samples can be arranged. A sample vessel can be a test tube, a blood collecting vessel, or any other vessels that can store a sample.

Figure 2:
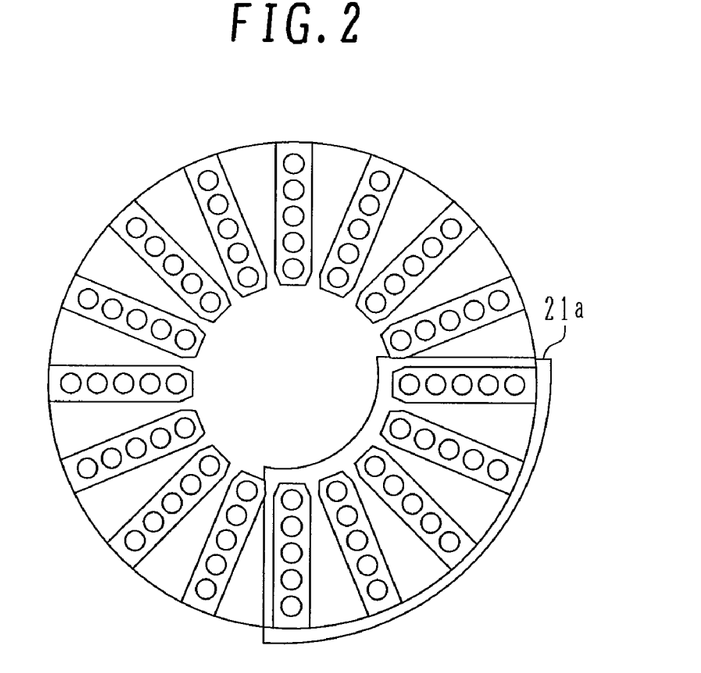
FIG. 2 is a diagram showing an area which holds a precision control sample of the automatic analyzer according to the present invention.
Figure 3:
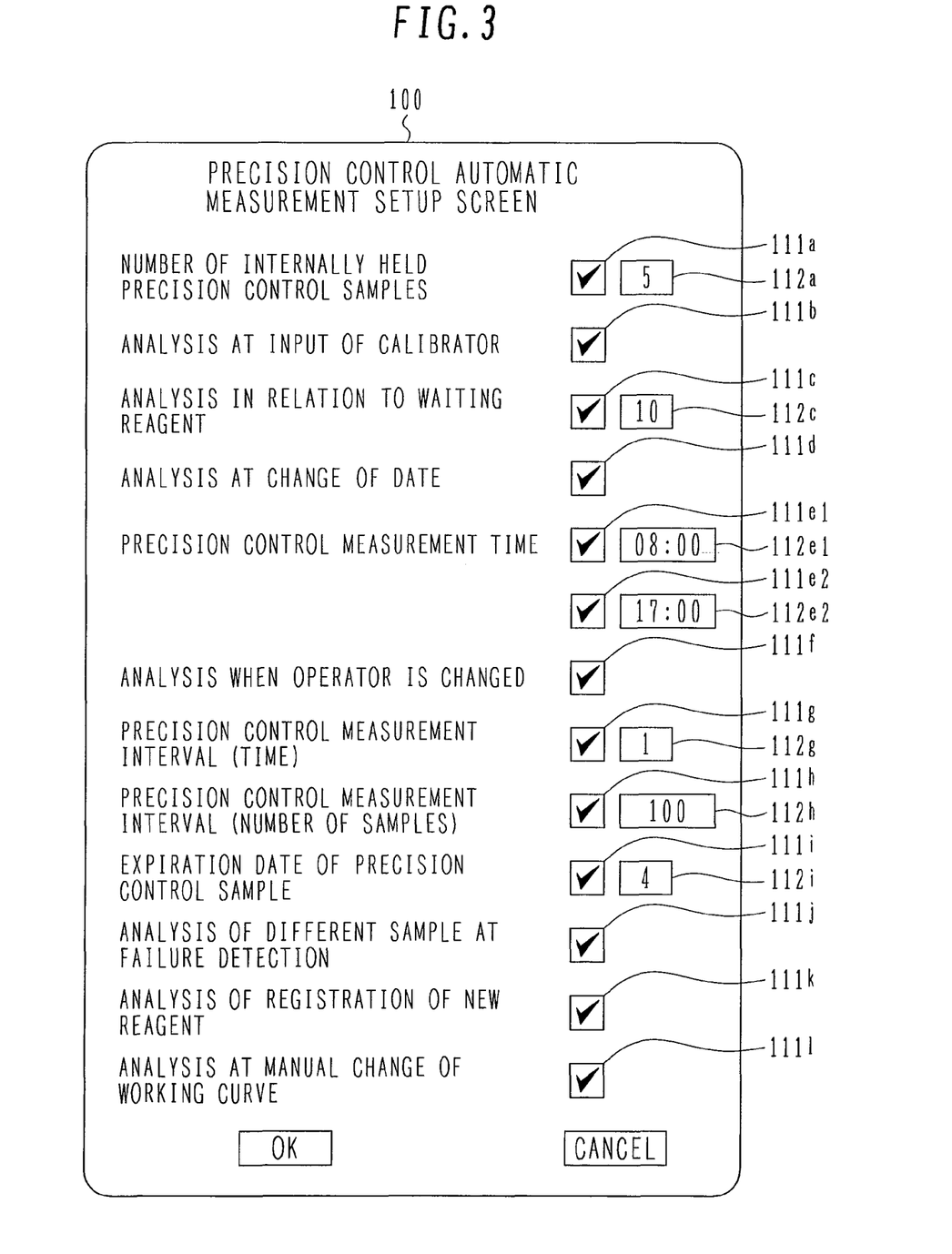
FIG. 3 is a diagram showing a screen for registering various setups for an internally held precision control sample in the automatic analyzer according to the present invention.
Figure 4:
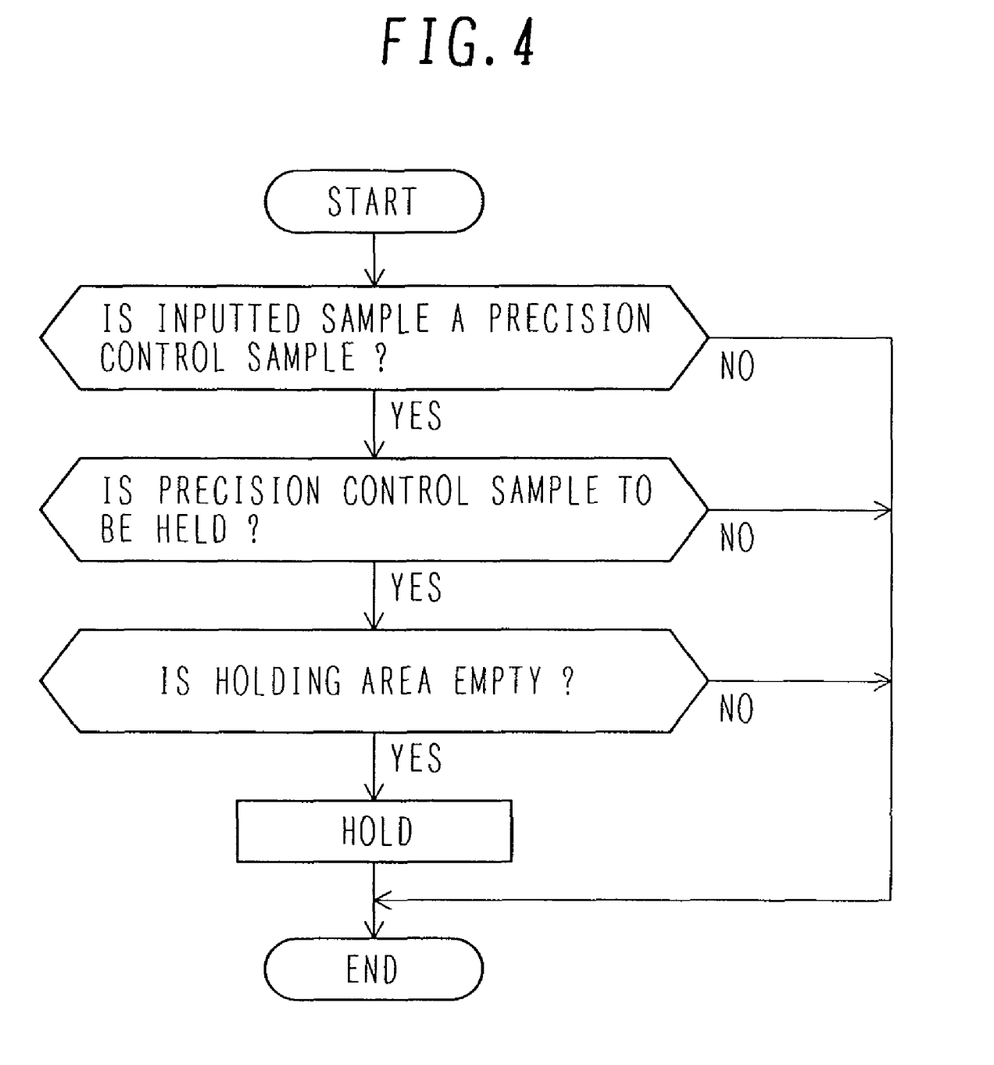
FIG. 4 is a diagram showing a processing flow when a precision control sample to be held internally in the automatic analyzer according to the present invention.

The following explains processing for internally holding a precision control sample in the automatic analysis system according to the present embodiment, with reference to FIGS. 2, 3, and 4.

When a rack from the sample rack input part 10, the sample type is determined from the sample ID and the sample rack ID read by the ID reader 12.

In this case, if a recognized sample rack arranges a precision control sample, if holding is set with setup of holding of precision control samples 111a, if number of internally held precision control samples 112a is 1 or above, and if a precision control sample hold area 21a is empty, the sample is held in the analyzer for each rack.

If the sample is not a precision control sample or if the setup is disabled, the sample is subjected to normal analysis and then collected in the sample rack storage part 11 as usual.

Figure 5:
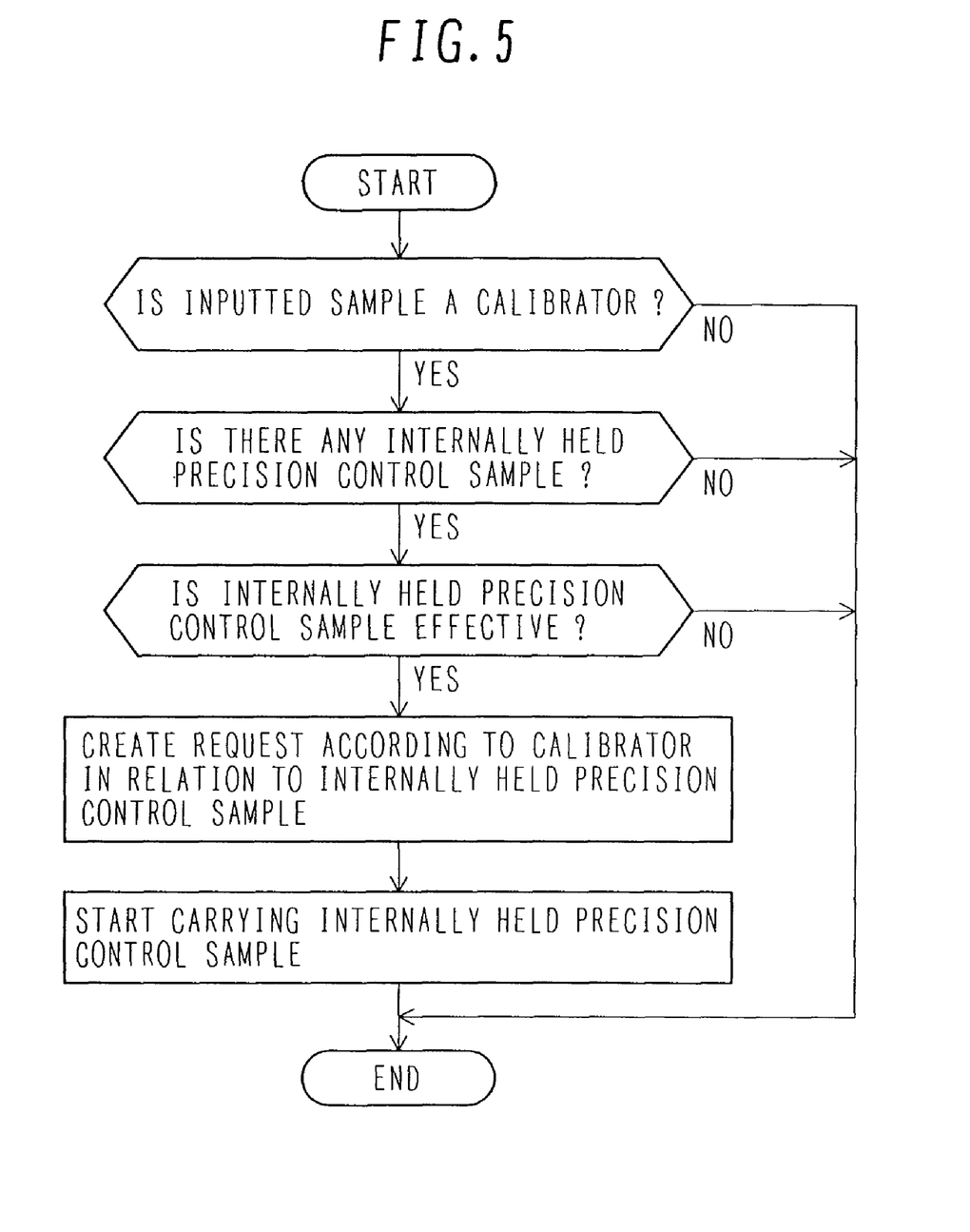
FIG. 5 is a diagram showing a processing flow for performing precision control by use of a precision control sample to be held internally when a calibrator in the automatic analyzer according to the present invention.

The following explains analysis of an internally held precision control sample with input of a calibrator in the automatic analysis system according to the present embodiment, with reference to FIG. 5.

As mentioned above, when the sample type is determined by the sample ID and the sample rack ID read by the ID reader 12, if the sample type is recognized as a calibrator and if an effective precision control sample is held in the analyzer, an analysis request for a predetermined item (for example, the same item) is created for an item to be analyzed with a calibrator in relation to the precision control sample.

After a calibrator is transferred, internally held precision control samples are transferred in succession and then measured.

If the sample is not a calibrator or if no effective precision control sample is held, only the calibrator is subjected to normal measurement processing.

The above-mentioned analysis makes it possible to perform measurement of a precision control sample based on a calibrator. Therefore, it becomes possible for the operator to omit the creation of an analysis request for a precision control sample and the preparation of a sample.

Figure 6:
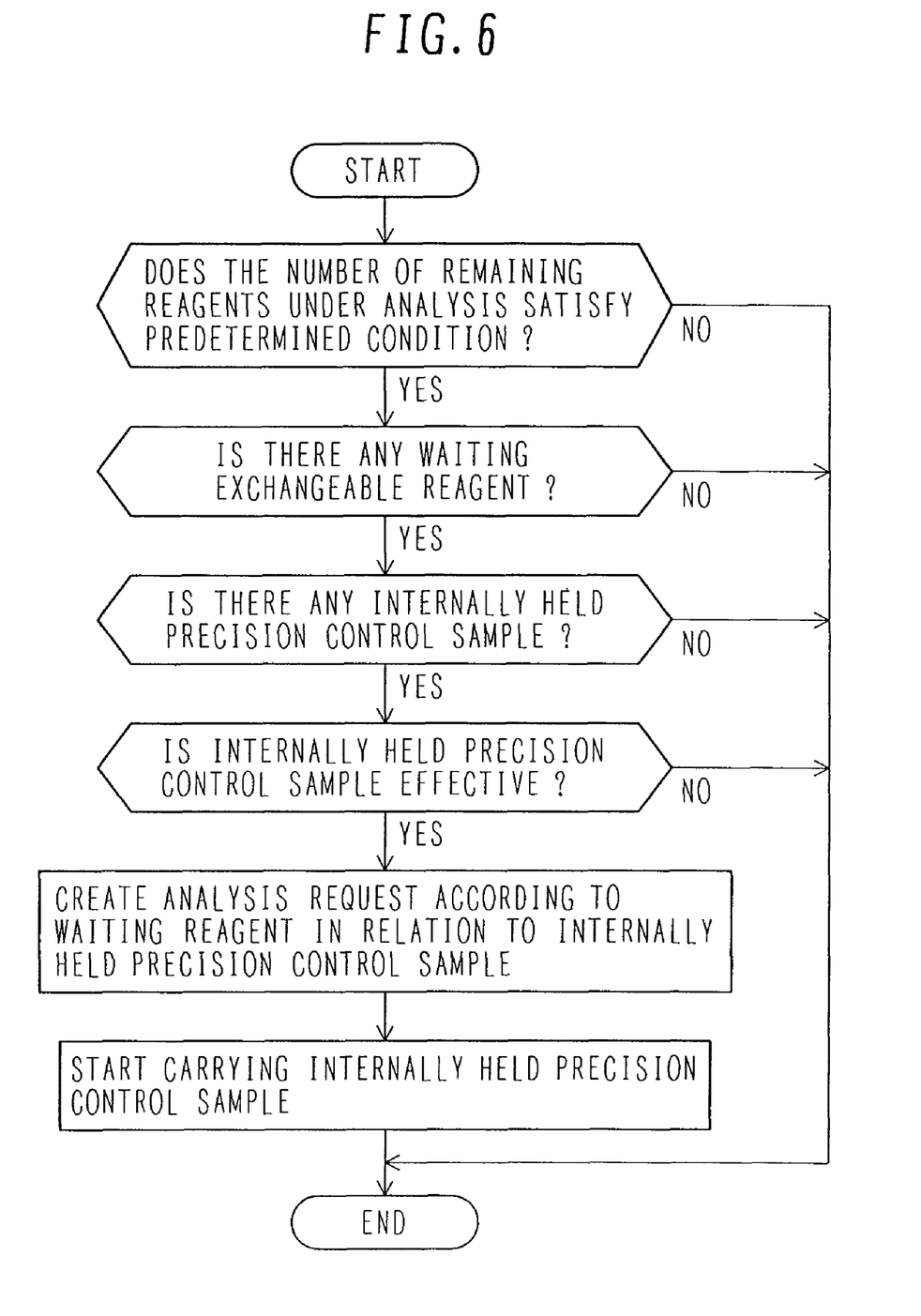
FIG. 6 is a diagram showing a processing flow for performing precision control by use of a precision control sample to be held internally when the number of remaining reagents satisfies a predetermined condition when reagents are used in the automatic analyzer according to the present invention.

The following explains analysis of an internally held precision control sample in relation to a waiting reagent in the automatic analysis system according to the present embodiment, with reference to FIG. 6. With the present embodiment, assuming an automatic analyzer in which a waiting reagent is automatically selected when the number of remaining reagents currently being used becomes zero, the following explains a case where measurement of a precision control sample is automatically performed when the number of remaining reagents falls below a threshold value.

With a rack holding a sample, which is assigned an analysis item and transferred to the analysis modules 31 and 32, the sample will be dispensed in order to analyze the item.

At this timing, analysis of the item is started and, when reagents from the analysis modules 31 and 32 have been consumed, the update of the number of remaining analyzable reagents is reported and then the total management computers 1 and 2 update the number of analyzable reagents.

In this case, if it is determined that the updated number of remaining analyzable reagents falls below the number of remaining analyzable reagents designated in Waiting reagent analysis condition 112c at this time, if a reagent that can be replaced in relation to the inspection item is waiting, and if there is an internally held precision control sample, a predetermined analysis request is created in relation to an internally held precision control sample, the internally held precision control sample is transferred, and analysis is performed.

If the updated number of remaining analyzable reagents does not fall below the number of remaining analyzable reagents designated in Waiting reagent analysis condition 112c, if no reagent that can be replaced in relation to the inspection item is waiting, or if there is no internally held precision control sample, analysis of the precision control sample is not performed.

This makes it possible to perform measurement of the precision control sample immediately before the waiting reagent is selected, thereby making it easier to maintain the measurement precision of the inspection item.

Figure 7:
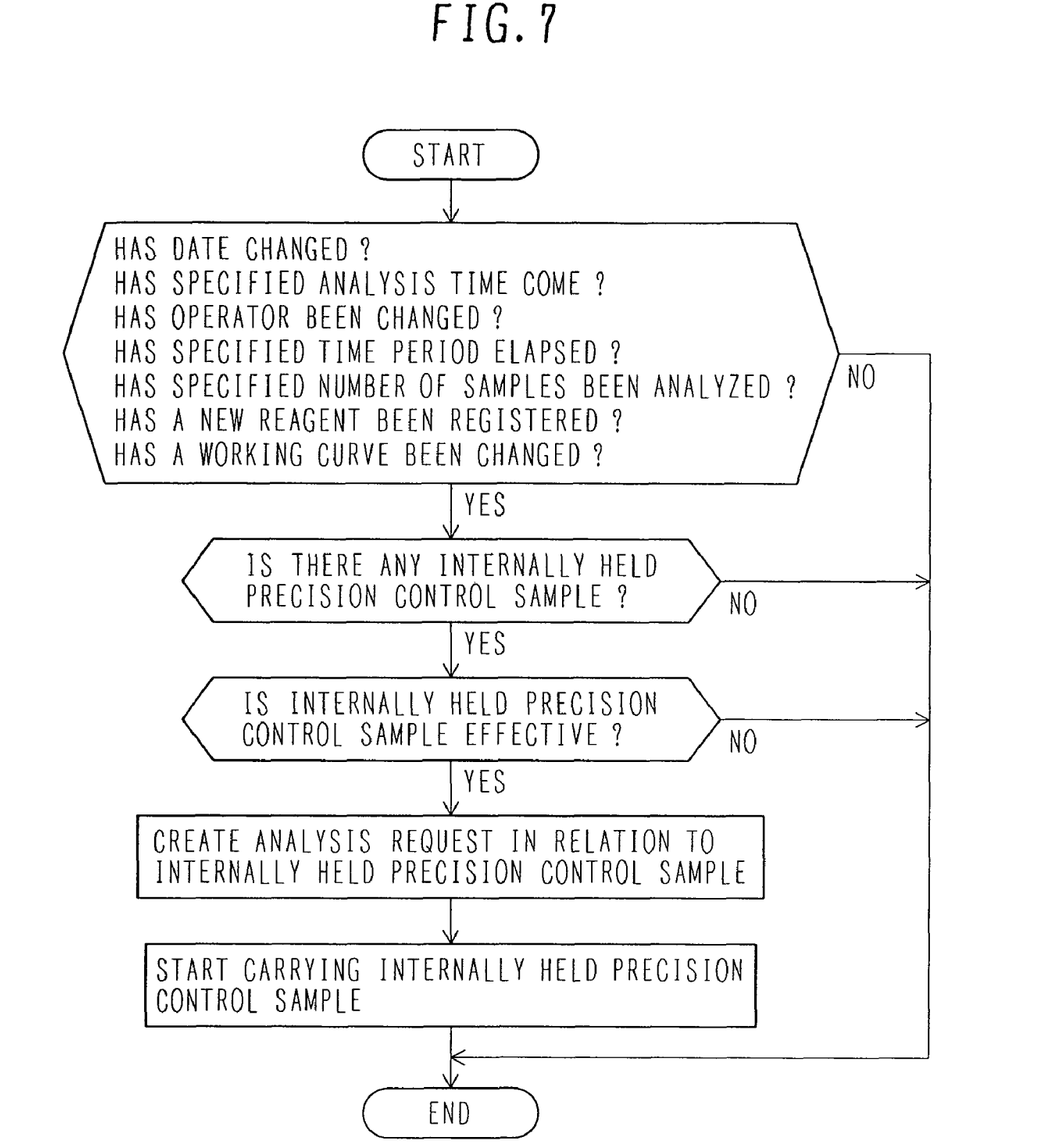
FIG. 7 is a diagram showing a processing flow for performing precision control by use of a precision control sample to be held internally when each condition is satisfied in the automatic analyzer according to the present invention.

The following explains analysis on each condition with an internally held precision control sample in the automatic analysis system according to the present embodiment, with reference to FIG. 7.

If the date changes when setup of measurement at change of date 111d is enabled, if specified time 112e1 or 112e2 runs out when setup of measurement at specified time 111e1 or 111e2 is enabled, if the operator is changed when setup of measurement at change of operator 111f is enabled, if time interval 112g has elapsed since the last measurement time when setup of measurement at time intervals 111g is enabled, if the number of patient samples that has been measured since the last measurement of precision control exceeds number of samples 112h when setup of measurement by the number of samples 111h is enabled, if a new reagent is registered when setup of measurement at registration of new reagent 111k is enabled, or if an analytical curve is manually changed when setup of measurement at manual change of analytical curve 111l is enabled, a predetermined analysis request is created, an internally held precision control sample is transferred, and analysis is performed.

This makes it possible to perform measurement of a precision control sample under each condition. Therefore, it becomes possible for the operator to perform measurement of a precision control sample at appropriate timing without creating a request for a precision control sample and preparing a sample.

Figure 8:
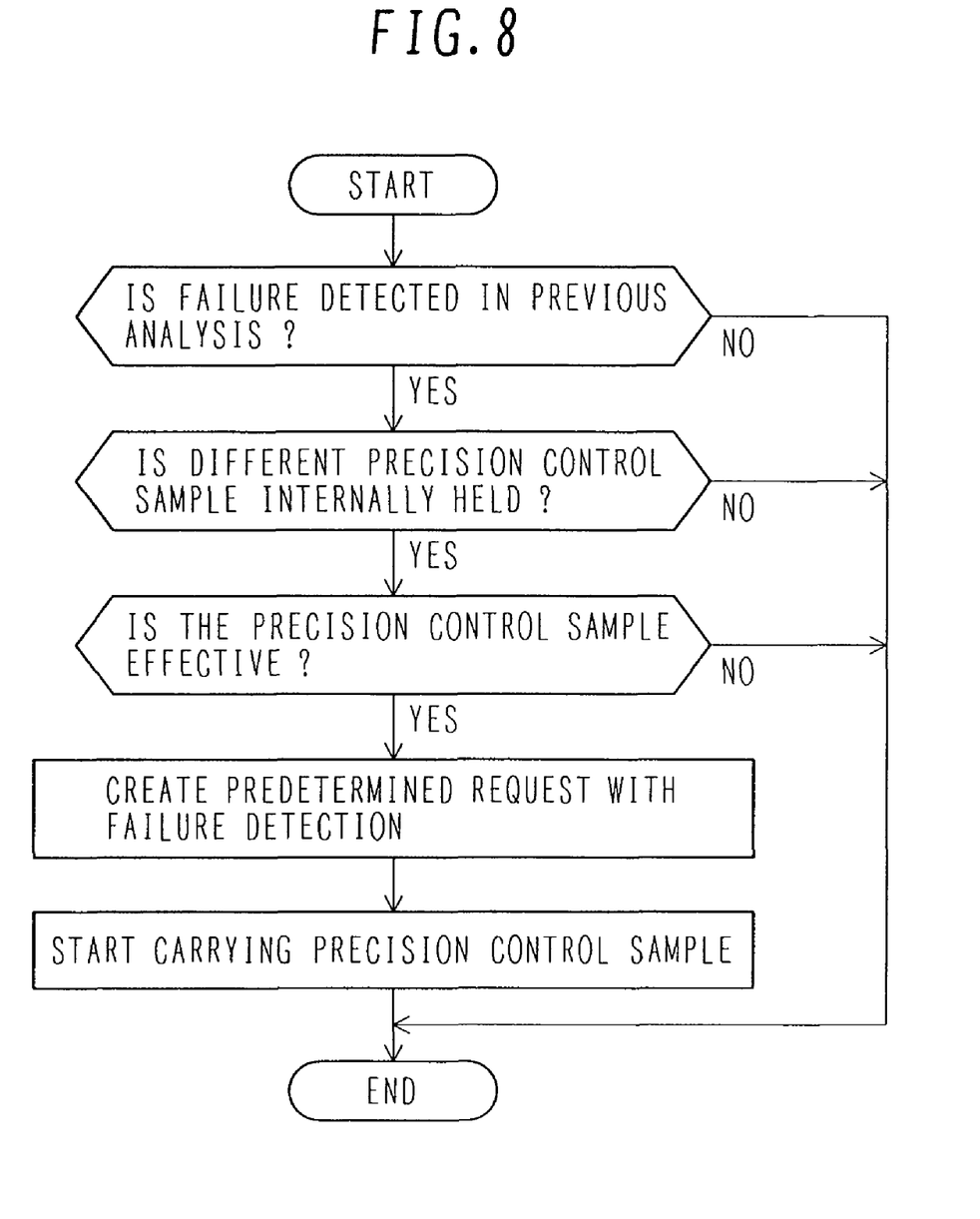
FIG. 8 is a diagram showing a processing flow for performing precision control by use of a precision control sample to be held internally when measurement failure is detected in the automatic analyzer according to the present invention.

The following explains analysis with different internally held precision control samples based on failure detection at the time of precision control measurement in the automatic analysis system according to the present embodiment, with reference to FIG. 8.

If the precision control sample itself is deteriorated at the time of measurement of a precision control sample, the concentration may have changed and accordingly measurement results may indicate an abnormal value. In this case, if another precision control sample is held in the analyzer, which allows analysis of a requested item with which an abnormal value is detected with the precision control sample, when setup of measurement with different sample at failure detection 111j is enabled, the requested item is created for another internally held precision control sample, the precision control sample is transferred, and analysis is performed.

This makes it possible to determine whether the measurement item with abnormal value detection is really abnormal or the precision control sample itself with abnormal value detection is deteriorated.

Figure 9:
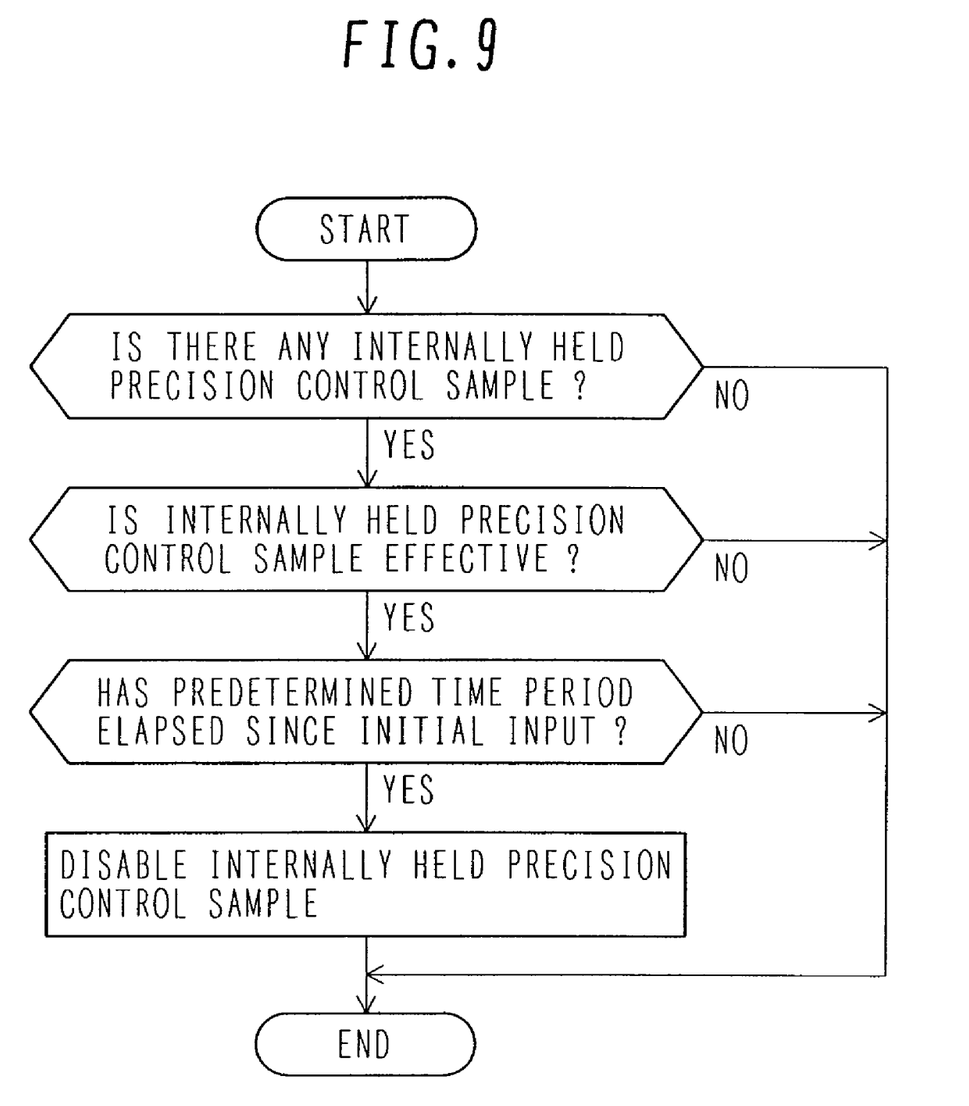
FIG. 9 is a diagram showing a processing flow when an expiration date of an internally held precision control sample has expired in the automatic analyzer according to the present invention.

The following explains expiration date control of an internally held precision control sample in the automatic analysis system according to the present embodiment, with reference to FIG. 9.

Generally, a precision control sample is provided with an expiration date. When the expiration date has expired, some components of the sample may vary making it impossible to acquire an expected concentration value. This is why it is necessary to provide and control an expiration date for the sample. The expiration date depends on components, i.e., samples.

Further, since some samples are subjected to a few component variations, it is also assumed that a sample may have been consumed before component variation occurs while it is internally held. Therefore, it is also possible to make setting so as not to perform expiration date control.

The time when a precision control sample is stored in the management computers 1 and 2, and when the present time exceeds Precision control sample expiration date 112i, the precision control sample is disabled so as to be unusable. Subsequently, it becomes possible to inhibit analysis with a deteriorated precision control sample by making the precision control sample unusable.

Although the above has explained a case of an automatic analyzer in which a precision control sample is internally held by arranging it in a rack, similar control applies also to a case where a precision control sample is provided in the second sample provision unit of each analysis unit.

If the operator prepares a precision control sample in advance, it becomes possible to perform analysis of the precision control sample in response to an external factor, thereby alleviating the burden on the operator. Further, it becomes possible to surely perform precision control at appropriate timing at which precision control must be performed, thereby allowing automatic maintenance of the measurement precision.

What is claimed is:

1. An automatic analyzer comprising:
   an analysis unit for analyzing a sample;
   a rack transfer system for transferring a sample rack containing a sample vessel which holds the sample to the analysis unit;
   a rack input slot for inputting a sample rack to the rack transfer system; and
   a sample rack buffer unit for internally holding a precision control sample in the analyzer, the precision control sample being provided in the sample rack; and
   control means configured to automatically create, if a measurement result using a precision control sample in relation to a requested item of a sample being analyzed is abnormal, a request for another predetermined measurement of the requested item using a different internally held control sample and to then transfer the different control sample and perform another measurement.

2. The automatic analyzer according to claim 1, further comprising:
   a cooling mechanism for cooling a precision control sample held in the buffer unit.

3. The automatic analyzer according to claim 2, further comprising:
   a temperature increasing mechanism for temporarily increasing the temperature of a precision control sample in the buffer unit so that the quality of the precision control sample does not deteriorate by condensation produced by being taken out to a part of the analyzer which is not cooled from the cooling division.

4. The automatic analyzer according to claim 1, further comprising:
   a second holding mechanism for holding the precision control sample in a second sample providing part in the analysis unit which is different from the rack.

* * * * *